United States Patent

Glass

[19]

[11] Patent Number: 5,565,365
[45] Date of Patent: Oct. 15, 1996

[54] ASSAY FLOW APPARATUS AND METHOD

[75] Inventor: Thomas R. Glass, Idaho City, Id.

[73] Assignee: Sapidyne, Inc., Boise, Id.

[21] Appl. No.: 437,969

[22] Filed: May 10, 1995

Related U.S. Application Data

[63] Continuation of Ser. No. 215,515, Mar. 22, 1994, abandoned, which is a continuation of Ser. No. 26,507, Mar. 4, 1993, abandoned.

[51] Int. Cl.$^6$ .................................................. G01N 33/553
[52] U.S. Cl. ........................ 436/526; 436/501; 436/810; 422/311; 422/101; 210/695; 210/222
[58] Field of Search ................................ 422/56, 60, 99, 422/101, 82.08, 311; 436/501, 161, 810, 526; 210/198.2, 263, 223, 290, 291, 656, 679, 222, 695; 204/155; 209/213, 214

[56] References Cited

U.S. PATENT DOCUMENTS

| | | | |
|---|---|---|---|
| 1,716,321 | 5/1927 | Pearson | 359/665 |
| 2,798,718 | 10/1951 | Gross | 267/161 |
| 3,002,092 | 9/1961 | Cary | 250/351 |
| 3,025,142 | 3/1962 | Williams | 436/111 |
| 3,492,396 | 1/1970 | Dalton et al. | 210/198.2 X |
| 3,600,063 | 8/1971 | Bowen | 359/626 |
| 3,740,552 | 6/1973 | Pressman | 250/423 P |
| 4,059,685 | 11/1977 | Johnson | 436/533 |
| 4,153,675 | 5/1979 | Kleinerman | 436/518 |
| 4,173,392 | 11/1979 | Ekinaka et al. | 385/117 |
| 4,201,831 | 5/1980 | Slusarczuk et al. | 210/679 X |
| 4,268,171 | 5/1981 | Sternberg | 436/517 |
| 4,314,905 | 2/1982 | Etzel et al. | 210/223 X |
| 4,348,107 | 9/1982 | Leif | 356/72 |
| 4,425,438 | 1/1984 | Bauman et al. | 436/527 |
| 4,454,234 | 6/1984 | Czerlinski | 436/526 |
| 4,469,787 | 9/1984 | Woods et al. . | |
| 4,495,074 | 1/1985 | Hagiuara et al. | 210/223 X |
| 4,505,260 | 3/1985 | Metzger | 126/637 |
| 4,582,809 | 4/1986 | Block et al. | 422/82.08 X |

(List continued on next page.)

FOREIGN PATENT DOCUMENTS

| | | |
|---|---|---|
| 1152898 | 8/1983 | Canada . |
| 0206077 | 6/1986 | European Pat. Off. . |
| 0317286 | 11/1988 | European Pat. Off. . |
| 404258 | 6/1990 | European Pat. Off. . |
| 1507421 | 5/1987 | U.S.S.R. . |
| 1572678 | 5/1988 | U.S.S.R. . |
| 1439175 | 5/1973 | United Kingdom . |
| 81/02529 | 3/1981 | WIPO . |
| 87/01608 | 9/1986 | WIPO . |
| 87/05003 | 2/1987 | WIPO . |
| 90/07380 | 7/1990 | WIPO . |

OTHER PUBLICATIONS

Friguet et al., "Measurements of the true affinity constant in solution of antigen–antibody complexes by enzyme-linked immunosorbent assay", Jour. of Immun. Methods, 77, pp. 305–319, 1985.

Plant et al., "Liposome-Enhanced Flow Injection Immunoanalysis"., *Biotechnology*, vol. 6., Mar. 1988., pp. 266–269.

Sato et al., "A Novel Method for Isolating Specific Endocytic Vesicles Using Very Fine Ferrite Particles Coated With Biological Ligands and the High–Gradient Magnetic Separation Technique"., *J. Biochem.*, vol. 100; No. 6., 1986; 1481–1492.

(List continued on next page.)

*Primary Examiner*—Robert Warden
*Assistant Examiner*—Theresa T. Snider
*Attorney, Agent, or Firm*—Choate, Hall & Stewart

[57] ABSTRACT

A system for assaying a fluid sample by detection of radiation emitted from a ligand/conjugate complex formed on a plurality of beads dimensioned within a specified range of diameters, the beads being disposed as a porous mass in a conduit adjacent a fluid-porous screen having pores of lesser diameter than the range of diameters of the beads. A plurality of paramagnetic particles is suspended across the conduit by a magnetic field of sufficient intensity to array the paramagnetic particles as the fluid-porous screen.

18 Claims, 2 Drawing Sheets

U.S. PATENT DOCUMENTS

| | | |
|---|---|---|
| 4,585,623 | 4/1986 | Chandler .................................. 422/57 |
| 4,652,533 | 3/1987 | Jolley ........................................ 435/5 |
| 4,668,591 | 5/1987 | Minemura ............................... 428/605 |
| 4,678,268 | 7/1987 | Russo et al. ............................ 359/642 |
| 4,713,347 | 12/1987 | Mitchell et al. ........................ 436/501 |
| 4,714,345 | 12/1987 | Schrader ................................. 356/246 |
| 4,738,773 | 4/1988 | Müller-Ruchholtz et al. ......... 209/214 |
| 4,775,515 | 10/1988 | Cottingham .............................. 422/73 |
| 4,780,423 | 10/1988 | Bluestein et al. ....................... 436/527 |
| 4,895,650 | 1/1990 | Wang .................................. 422/101 X |
| 4,912,051 | 3/1990 | Zaromb ................................... 436/178 |
| 4,963,498 | 10/1990 | Hillman et al. ........................... 436/69 |
| 5,110,624 | 5/1992 | Noble et al. ........................ 210/223 X |
| 5,110,727 | 5/1992 | Oberhardt ................................. 435/13 |
| 5,120,643 | 6/1992 | Ching et al. ............................ 435/7.92 |
| 5,183,486 | 2/1993 | Gatten et al. ..................... 210/198.2 X |
| 5,183,740 | 2/1993 | Ligler et al. ........................... 435/7.32 |
| 5,372,783 | 12/1994 | Lackie .................................... 422/68.1 |

OTHER PUBLICATIONS

Gunaratna et al., "Noncompetitive flow injection immunoassay for a hapten, α–(Difluoromethyl)ornithine", Anal. Chem, 1993, 65, pp. 1152–1157.

G. Gübitz et al., "Flow–injection immunassays", Analytica Chimica Acta, 283, 1993, pp. 421–428.

Pollema et al., "Flow injection renewable surface immunoassay: a new approach to immunoanalysis with fluorescence detection", Anal. Chem., 1994, pp. 1825–1831.

Sambucetti et al., "Process For Purification of Magnetic Ink", IBM Technical Disclosure Bulletin, vol. 18, No. 2, Jul. 1975.

Freytag et al., "Affinity–Column–Mediated Immunoenzymometric Assays: Influence of Affinity–Column Ligand and Valency of Antibody–Enzyme Conjugates", Clin. Chem., V. 30, No. 9, 1494–1498, 1984.

Freytag et al., "A Highly Sensitive Affinity–Column–Mediated Immunometric Assay, as Exemplified by Digoxin", Clin. Chem., V. 30, No. 3, 417–420, 1984.

O'Shannessy et al., "Determination of Rate of Equilibrium Binding Constants for Macromolecular Interactions Using Surface Plasmon Resonance: Use of Nonlinear Least Squares Analysis Methods", Anal. Biochem, V. 212, 457–468, 1993.

Ralf W. Glaser, "Antigen–Antibody Binding and Mass Transport by Convection and Diffusion to a Surface: A Two–Dimensional Computer Model of Binding and Dissociation Kinetics", Anal. Biochem., V. 213, 152–161, 1993.

Warren J. Smith, "Modern Optical Engineering. The Design of Optical Systems", McGraw–Hill, Inc. (pubs) ©1966.

Hudson, "Infrared Systems Engineering", Wiley–Interscience, 1969.

Pollema et al., "Sequential Injection Immunoassay Utilizing Immunomagnetic Beads", Anal. Chem., vol. 64, 1356–1361, 1992.

Forrest, "Development and Application Of A Fully Automated Continous Flow Radioimmunoassay System", Ann. Clin. Biochem., V. 14, 1–11, 1977.

M. E. Jolley et al., "Particle Concentration Fluorescence Immunoassay (PCFIA); A New Rapid Immunoassay Technique with High Sensitivity", Journal of Immunological Methods, vol. 67, 21–35, 1984.

ASSAY FLOW APPARATUS AND METHOD

FIELD OF THE INVENTION

This application is a Continuation of U.S. patent application Ser. No. 08/215,515, filed Mar. 22, 1994, now abandoned, which is a Continuation of U.S. application Ser. No. 08/026,507, filed Mar. 4, 1993, now abandoned; each of which is hereby incorporated by reference.

BACKGROUND OF THE INVENTION

This invention relates to chemical and biochemical assays, and more particularly to an improved optical apparatus and methods for radiation-emitting assays.

Assays are well known in which aliquots of sample-under-test one or more reagents are variously reacted in highly specific reactions to form ligand/conjugate complexes such as antigen/antibody or similar complexes which may then be observed in order to assay the sample for a titer of a predetermined moiety from the sample. Typically, an antibody is used to assay for the presence of an antigen for which the antibody is specific, but such assays have been extended to quantitate haptens such as hormones, alkaloids, steroids, antigens, antibodies, nucleic acids, and fragments thereof. It is in this broad sense that the term "ligand/conjugate" as used herein should be understood.

Sensitive immunoassays typically use tracer techniques in which a tagged constituent of the complex is incorporated, for example in the reagent, the non-complex tagged reagent then being separated from the complexed reagent. The complex can be thereafter quantitated by observing a signal from the tag. Radioisotopes, fluorescent and chemiluminescent molecules, colorimetric tags, and other radiation-emitting markers have been used to label constituents or moieties of the complex, appropriate apparatus being employed to detect and measure the radiation from the label.

In such assays where at least one component of the conjugate complex is initially bound to a solid substrate preparatory to formation of the complex, a basic problem arises because of the typically lengthy time required to bind that component to the substrate. For example, fluorescent assays such as those performed in the usual 96 well microtiter plate, require time in the order of hours to effect binding of a component to the solid phase, despite such expedients as heating, shaking and the like. The binding delay may be considerably reduced by increasing the surface area of the solid phase made available to binding or coating with a ligand. Flowing the sample through a packed particulate bed speeds reactions between the sample ligand being assayed and a conjugate immobilized on the surface of the particles.

Consequently, in U.S. patent application Ser. No. 07/924,720 filed Aug. 3, 1992, now U.S. Pat. No. 5,372,783, there is disclosed, inter alia, a flow cell for use in apparatus for assaying a fluid sample, the flow cell comprising a hollow, light-transparent conduit through which a fluid sample being assayed can flow. A fluid-porous barrier or screen is emplaced within the conduit so as to define at least one wall of a chamber in which there is disposed a porous mass comprising a plurality of light-transparent particles dimensioned within a specified range of diameters, the particles having immobilized on their surfaces at least a moiety of a ligand/conjugate complex. The porosity of the screen is sufficiently smaller than such range so that the particles are trapped by the screen and the porosity of the mass of transparent particles is selected so as to permit fluid flow of the sample therethrough. The conduit is preferably disposed within a lens so as to extend transversely to the optical axis of the lens through the focal region of the latter.

While this flow cell has been effective to reduce binding delays and speed reaction times between the sample ligand and the immobilized moiety of a ligand/conjugate complex, there is nonetheless an unfortunate tendency for the screen to become plugged with a gelatinous material after several cycles of use with whole blood as the sample, impeding flow and causing assay errors. Changing the material of the screen, for example to relatively non-stick materials such as polytetrafluorethylene, or cleaning the screen with a variety of solvents such as bases, acids, alcohols, detergents and the like did not provide a satisfactory solution.

SUMMARY OF THE INVENTION

A principal object of the present invention is therefore to provide an improved assay system of the type described in which the problems of plugging are overcome by providing a readily replaceable screen. Other objects of the present invention are to provide such a system in which the screen itself is formed of immunologically active elements, and to provide such a system that is particularly suitable for assay of whole blood.

Other objects of the present invention will in part be obvious and will in part appear hereinafter. Generally, the foregoing and other objects of the present invention are achieved by a system for assaying a fluid sample, typically employing a tag or label intended to emit electromagnetic radiation when excited, the system comprising a flow cell comprising a hollow conduit, at least a portion of which is light-transparent, adapted for fluid flow therethrough, and a fluid-porous barrier or screen disposed in the conduit and formed and maintained by a magnetic field. In one embodiment, the barrier is established and maintained within the conduit by means for establishing a magnetic field exhibiting a gradient of flux density, typically extending transversely to the axis of elongation of the conduit, sufficient to cooperate with a plurality of paramagnetic particles (which term, as used herein is intended to embrace all materials having a magnetic permeability greater than unity, and therefore includes particularly ferromagnetic materials) to create a barrier. The barrier created from such paramagnetic particles thereby defines at least one wall of chamber for confining a mass of radiation-emitting particles within the conduit. The porosity of such mass of radiation-emitting particles is selected to permit fluid flow of the sample therethrough, at least a moiety of a respective ligand/conjugate complex e.g. a specific-binding ligand, being immobilized, as by precoating, on the surfaces of the radiation-emitting particles within the mass. The sizes of the paramagnetic particles are selected so that the porosity of the barrier is sufficiently smaller than the range of sizes of the radiation-emitting particles so that latter particles entrained in a fluid flow through the conduit become trapped by the barrier and accrete to form the porous mass in the chamber.

In one embodiment, the porous mass comprises a plurality of particles preferably substantially transparent to light (the latter term, as used herein, being intended to include any form of electromagnetic radiation emitted from a label or tag, including but not limited to infra-red, visible, ultraviolet and other higher energy quanta). Particularly, where the complex formed includes a fluorescent label, the plurality of radiation-emitting particles should be transparent to both radiation required to excite fluorescence and the excited fluorescent radiation. The particles are typically beads dimensioned within a specified range of diameters and can be preformed, as by sintering or the like.

In yet another embodiment of the present invention, the radiation-emitting particles are reflective or translucent. In still another embodiment of the present invention, the paramagnetic particles are themselves precoated with an immobilized moiety of a ligand/conjugate complex, and may be reflective, transparent or translucent.

The invention accordingly comprises the apparatus possessing the construction, combination of elements and arrangement of parts, and the method comprising the several steps and the relation of one or more of such steps with respect to each of the others, all as exemplified in the following disclosure, and the scope of the application of which will be indicated in the claims.

For a fuller understanding of the nature and objects of the present invention, reference should be had to the following detailed description taken in connection with the accompanying drawings in which like numerals in the several drawings are employed to denote like pans, and wherein:

DESCRIPTION OF THE PREFERRED EMBODIMENTS

Figure 1:
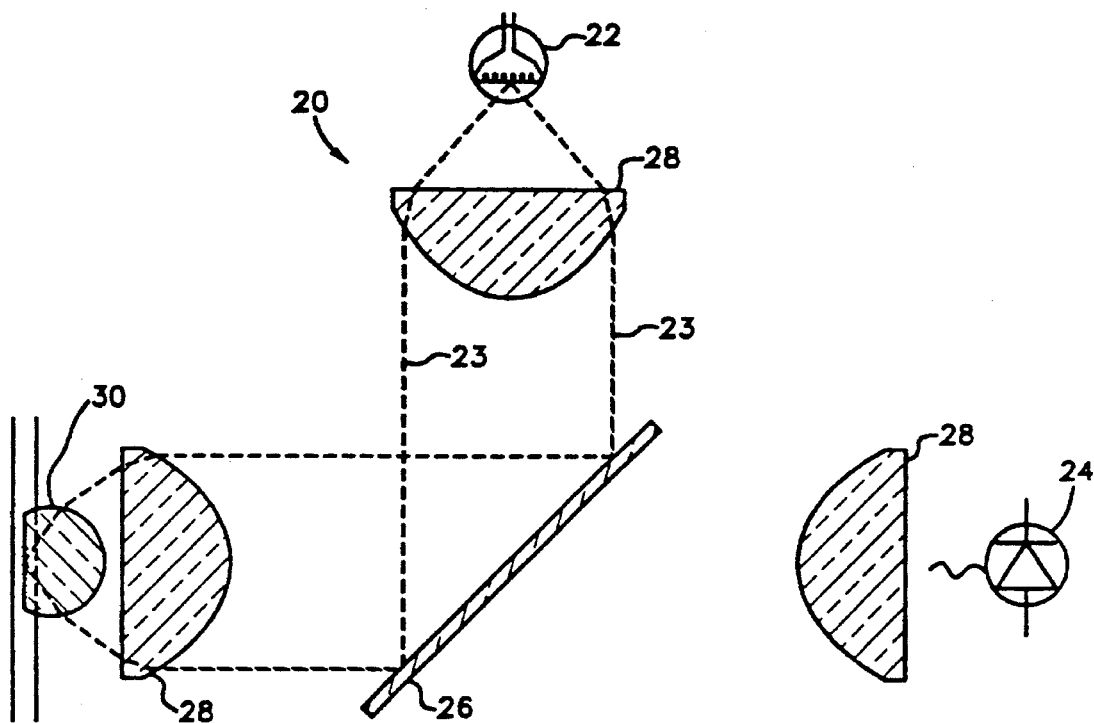
FIG. 1 is a diagrammatic representation, partly in cross-section, of assay apparatus embodying the principles of the present invention.

In FIG. 1 there is shown exemplary apparatus 20 for assaying a fluid sample and which may typically employ an optical system including light source 22 for providing excitation radiation if necessary, light detector 24 for detecting emitted light such as that stimulated by the excitation radiation, beam splitter means such as dichroic or semitransparent mirror 26 and collimator means 28. The embodiment of FIGS. 1 and 2 will be described, for ease of exposition, for use particularly in the context of fluorescence immunoassay, but it should be understood is not so limited. Similarly, the term "excitation" will be understood to include excitation of fluorescence, polarized or not, as by radiation, excitation of chemiluminescence by chemical agents, emission by reflection of light from chromogens, and the like.

The foregoing elements of the optical system are typically disposed in a frame (not shown) in fixed optical relationship to one another, as described more fully hereinafter. The present invention resides particularly in flow cell 30, shown particularly in enlarged form in FIGS. 2 and 3, which may, as described in the aforesaid U.S. patent application Ser. No. 07/924,720 now U.S. Pat. No. 5,372,783, be formed as part of focussing optical lens 32, typically made of glass, high molecular weight polymer or the like. In such case, flow cell 30 includes elongated hollow channel or fluid-flow conducting conduit 34 formed in lens 32 directed transversely to the optical axis of lens 32 and comprising a tubular passage, typically in circular cross-section, through lens 32. At least a portion of conduit 34, identified as reaction chamber 36 which is at least in part transparent, is disposed at the focal region of lens 32. Alternatively, other optical system, well known in the art, may be employed to gather radiation emitted from chamber 36 and transmit such radiation to detector apparatus for converting the radiation into electrical signals.

Thus, for example, the invention is employed to assay for a ligand in a fluid that traverses chamber 36, which fluid contains a radiation-emitting ligand that emits spontaneously as by radioactive decay or requires excitation to radiate per se or because of an appropriate tag. Assume that the fluid can be excited into fluorescence by radiation focussed onto chamber 36 by lens 32. That fluorescent emission is then directed by lens 32 to detector 24 where, assuming that the detector for example is electrical, appropriate electrical signals are produced and can be assessed to evaluate the fluorescence.

Figure 2:
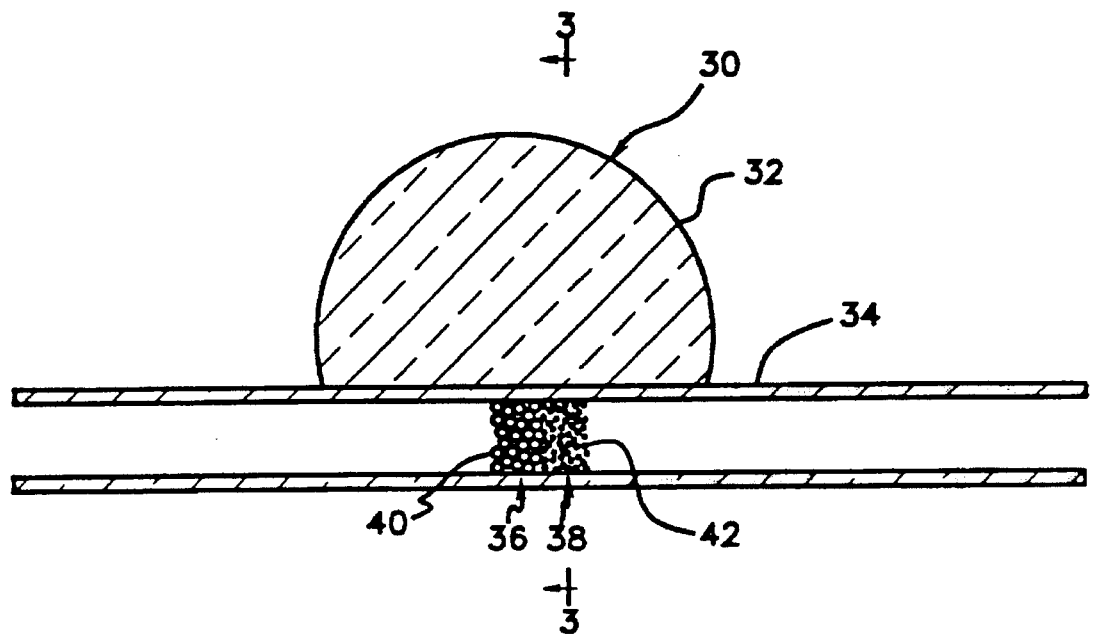
FIG. 2 is an enlarged view of a cross-section of the flow cell of FIG. 1 taken along the axis of elongation of the cell.
Figure 3:
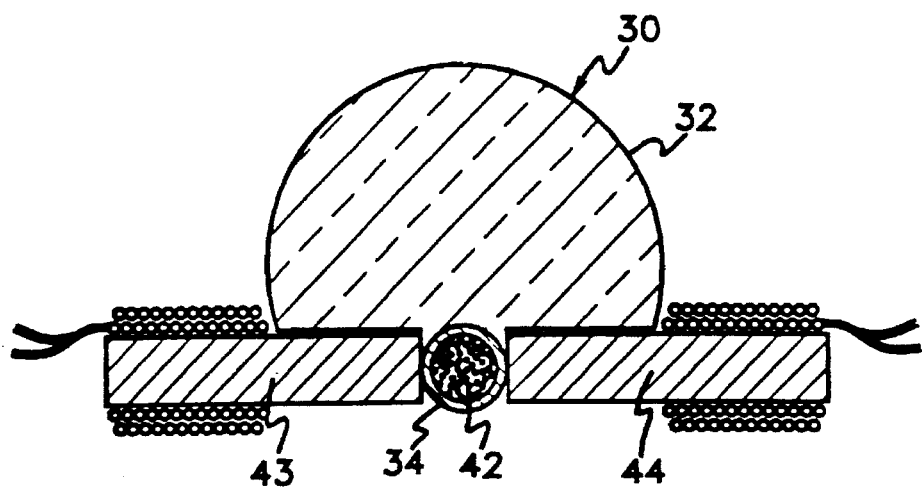
FIG. 3 is a transverse cross-sectional of the flow cell of FIG. 2 taken along the line 3—3 in FIG. 2.

In order to provide a better signal-to-ligand ratio, the embodiment shown in FIGS. 1–3 includes fluid-porous barrier or screen 38 dimensioned and disposed in conduit 34 adjacent the focal region of lens 32 so as to arrest transport of particles or beads 40 of predetermined size in a flow stream through the conduit. Such beads are typically substantially transparent to both the excitation radiation and the excited fluorescence, and to that end are typically formed of polymethylmethacrylate, styrene-divinylbenzene copolymer or the like. Alternatively, beads 40 can be formed of translucent or highly reflective material or the like. Beads 40 are coated with material that will react in highly specific reaction to form a ligand/conjugate complex with a suspected ligand in a sample being assayed, which complex may then be observed in order to assay the sample for a titer of a predetermined moiety from the sample. Typically, the coating can be at least a moiety of the antibody/antigen complex, e.g. a specific-binding ligand, for example an antigen and an antibody thereto, disposed at least on portions of the surfaces of the respective beads.

Screen 38 is formed by the cooperation of a plurality of paramagnetic particles 42 with magnetic means typified by a pair of magnets 43 and 44 disposed on opposite sides of reaction chamber 36 so as to produce a magnetic field through the latter transversely to the axis of elongation of conduit 34. As will be understood with reference to the drawings and the discussion herein, screen 38 spans the cross-sectional area of conduit 34. Furthermore, screen 38 is self-supporting (i.e. is maintained in conduit 34 without requiring additional mechanical support means). As shown in FIG. 2, screen 38 also supports beads 40 and retains them in conduit 34 against the flow of fluid therethrough. The magnetic field provided by magnets 43 and 44 is preferably substantially uniform within or adjacent chamber 36 and of sufficient intensity to cause particles 42, when the latter are introduced into chamber 36 typically in a flow stream of a carrier fluid, to agglomerate and form barrier or screen 38. Magnets 43 and 44 preferably have opposed, coaxial, planar pole faces so as to provide preferably uniformity of the magnetic field produced in the chamber. While it is preferred that magnets 43 and 44 be in the form of electromagnets so that the magnetic field thereof can be established at will, in a less expensive version, moveable permanent magnets can be employed. The magnets are typically narrow in the direction of elongation of robe 34 and wide in the transverse direction to thereby provide a large field gradient along the axis of tube 34 but a fairly uniform field across the tube.

The range of cross-section dimension of the beads is selected to provide a high mass to surface area ratio thereby yielding a large reaction surface and insuring that when a mass of such beads is accreted against screen 38, the sample constituents may still pass freely through the mass of beads. Typically, a bead size useful with whole blood as a sample is as small as 50 μm, and preferably around 98 μm. Bead size, of course, depends to some extent on the nature of the sample (e.g. blood, food, urine, process stream and the like). The porosity or mesh size of screen 38, of course, depends also upon the range of diameters of the beads to be employed in the system, and should be such that beads entrained in a fluid flow cannot pass through screen 38. Thus, as sample fluid is flowed through conduit 34, it must pass through the interstices of the accreted mass of coated beads 40, resulting in a very small diffusion distance over which the assayed moiety must pass to complex with the coating on the beads. This small diffusion distance, coupled with the long, tortuous path of the sample through the accreted mass and the high surface to volume ratio of the beads, enables very efficient scavenging of the assayed moiety from the sample.

In operation of the invention shown in FIGS. 1–3, an appropriate magnetic field is produced with respect to chamber 36 as by positioning magnets 43 and 44 on opposite sides of the chamber in close proximity thereto where magnets 43 and 44 are permanent magnets, or if magnets 43 and 44 are electromagnets, then by energizing same. Paramagnetic particles in sufficient quantity to form the desired screen 38 are suspended in an appropriate carrier fluid. Because the particles are quite heavy, it is preferred to suspend them, as by vortexing them in a viscous fluid such as a 50% sucrose solution, glycerol or the like. The suspended paramagnetic particles are then injected into conduit 34 where, traversing chamber 36, they are arrested by the magnetic field to form into screen 38. A quantity of beads 40, preferably preloaded with an appropriate ligand immobilized onto the bead surfaces by adsorption or other known immobilizing techniques, are suspended in a suspending carrier fluid. If the beads will ordinarily not readily form a stable suspension in the suspending fluid, they may be placed into a vortexer (not shown) or similar mixer which maintains the beads in a suspension, typically aqueous, by agitation. A desired portion of the bead suspension is sucked out of the vortexer as by a pump (not shown) and injected into conduit 34. The flow of the beads is arrested by screen 38, creating an accretion or mass of beads 40 within reaction chamber 36. An aliquot of sample solution being assayed is then flowed through conduit 34 and the mass of beads 40 in reaction chamber 36, effecting the formation of a ligand/conjugate complex on the surface of the beads. As is well known, for competitive assays, prior to flowing the sample solution through the flow cell, typically the sample solution is first treated with a tagging reagent and allowed to incubate. Where the assay is a sandwich assay, the sample solution is passed through the flow cell, then tagged antibody is passed through the cell, and the bead mass is subjected to a wash step. It is well known that a tagged, typically fluorescent, component may be either the complement or conjugate to or an analog of the immobilized ligand, depending upon whether a competitive or sandwich assay is to be performed. The tag or label is typically a fluorescent dye such as a fluorescein dye, acridine dye or the like, all as well known in the art. In either case, the resulting ligand/conjugate complex should include desired dye moieties bound to the complex. Flowing a wash buffer through the bead mass then washes out any unreacted materials and particularly any free dye components leaving only those dyed moieties as are immobilized on the beads. Light source 22 then activated to generate excitation light beam 23 (shown in broken lines) which turn, directed to mirror 26 by collimating lens 28 so that the collimated beam is reflected onto lens 32 along the optical axis of the latter. The lens focusses the excitation beam to a focal region at which the mass of beads 40 in reaction chamber 36 is located, and the excitation radiation excites the fluorophores on beads 40 into fluorescence. That fluorescence is transmitted through lens 32 and directed through beam splitter mirror 26 to detector 24. After measurements are made, the mass of beads 40 can be readily removed from reaction chamber 36 simply by back-flushing through conduit 34. Similarly, if interstices in screen 38 become plugged or impeded, removal of the magnetic field produced by magnets 43 and 44 will cause the accretion of paramagnetic particles to collapse and be washed out of chamber 36 with a forward flush or with the back flush.

Figure 4:
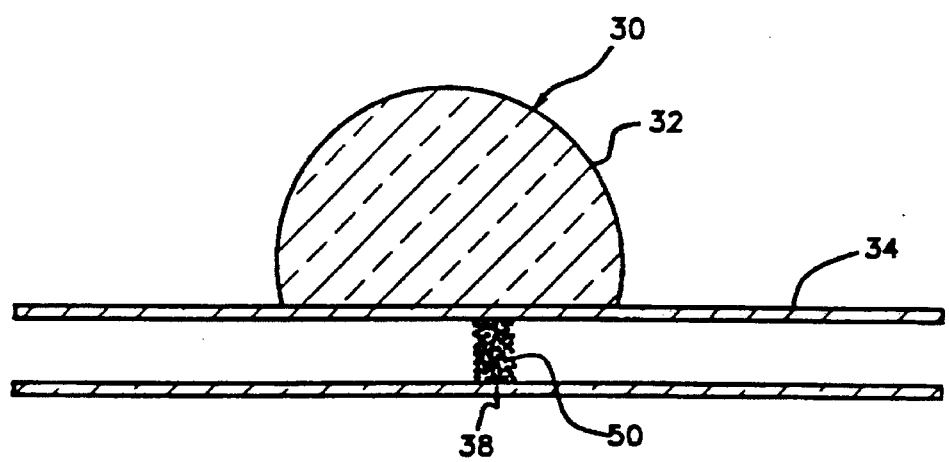
FIG. 4 is a enlarged axial cross-section of a variation of the flow cell of FIG. 1.

As shown in FIGS. 1 and 2, screen 38 and beads 40 are provided as separate entities, both of which are disposable. However, in the embodiment shown in FIG. 4, screen 38 is formed of particles 50 possessing paramagnetic properties and being themselves coated, at least in part, with at least a moiety of the antibody/antigen complex, e.g. a specific-binding ligand, for example an antigen and an antibody thereto. Thus, in processing a sample solution through the flow cell of FIG. 3, one can dispense with the separate steps of preparing two suspensions and flowing them seriatim through reaction chamber 36. Instead, one need only preload appropriate paramagnetic particles with an appropriate ligand immobilized onto the surfaces thereof as by adsorption or other known immobilizing techniques, and suspending such preloaded particles in a suspending carrier fluid. After creating the requisite, magnetic field in chamber 36, a flow of the preloaded paramagnetic particles through the chamber will form a screen that itself is, for example, immunologically active.

The operating of the present invention is shown in the following examples:

EXAMPLE I

A glass flow cell with a hollow internal conduit 34 having an internal diameter of 0.8 mm is provided on opposite sides thereof with a pair of coaxial electromagnets formed of ordinary steel 16d 3.5" nail shanks wound with 200 feet of 30 gauge, enamel insulated, copper wire. A suspension of 6 mg/ml of stainless steel power, Ancor 41OL, lot #62064/98 obtained from Hoeganaes Co., Riverton, N.J., is prepared in a sterile, aqueous solution of pH 7.4 phosphate-buffered saline solution (PBS). The composition of such powder, by weight, is 12.3% chromium, 0.9% silicon, 0.2% oxygen, about 0.05% impurities such as carbon, phosphorous, sulfur and nitrogen, the balance being iron, with a density of 2.74 g/cc. The powder, being passed by a #325 mesh, thus contains particles substantially no larger than 44 μm in diameter.

The electromagnet is turned off and the flow cell is flushed clean of all material using PBS. The electromagnets are then turned on to maintain a potential of 5 volts across the magnet windings, to create a magnetic field in a chamber in the conduit. The suspension of stainless steel power is injected into the conduit, forming a filter screen which readily retains polymethylmethacrylate (PMMA) beads of about 98 μm diameters.

For a ferritin assay, 200 milligrams of 98 μm PMMA beads are coated in 0.1 mg/ml sheep anti-horse ferritin antibody (Jackson Immunoresearch #508-005-063) in pH 7.4 PBS (Sigma #1000-3) for 1 hour at about 37° C. The coated PMMA beads are then blocked against non-specific binding using 10% normal sheep serum (Jackson #013@-

121) in PBS, again for 1 hour at about 37° C. The suspension of coated beads is then flowed into the flow cell to accrete as a mass against the porous screen formed from the stainless steel particles.

Sample solution is prepared from horse ferdti.n (Boehringer Mannheim #197 742) diluted to 500 ng/ml in PBS. Negative sample is PBS alone. A detection reagent is prepared using a fluorescein conjugated sheep anti-horse ferritin (Jackson Immunoresearch #508-095-063) diluted to 0.2 μg/ml in PBS. After the suspension of anti-horse ferritin antibody coated PMMA beads in PBS is flowed into the conduit and allowed to accrete against the stainless steel porous screen, sample solution either positive (containing ferritin) or negative, is flowed through the conduit. Where the sample is positive, horse ferritin is immobilized on the PMMA beads by binding to the anti-horse ferritin. The detection reagent of fluorescein-labeled anti-horse ferritin antibody is flowed through the conduit to bind to whatever immobilized horse ferritin is present. PBS is then flowed through the conduit to wash the beads and remove unbound labeled antibody.

It will be seen that this assay is a sandwich assay in which horse ferritin in the sample binds to the anti-horse ferritin on the coated beads and the second fluorescein labeled anti-horse ferritin binds to the immobilized horse ferritin.

Signal values in volts, arising from assays of both positive and negative samples, are taken as the endpoint reading (at the end of the wash) minus the baseline reading (before the sample), are shown in accompanying Table I from which it is clear that one is able to detect the presence of ferritin in the sample.

TABLE I

|      | Baseline | Endpoint | 0 ng/ml | 500 ng/ml |
|------|----------|----------|---------|-----------|
|      | 0.11745  | 0.175841 | 0.058391 |          |
|      | 0.112024 | 0.131954 | 0.01993 |           |
|      | 0.114169 | 0.167425 | 0.053256 |          |
|      | 0.112862 | 0.608749 |         | 0.495888  |
|      | 0.126377 | 0.61394  |         | 0.487563  |
|      | 0.141399 | 0.667735 |         | 0.526337  |
|      | 0.15479  | 0.630877 |         | 0.476087  |
|      | 0.163205 | 0.70628  |         | 0.543075  |
|      | 0.162061 | 0.202684 | 0.040623 |          |
|      | 0.151788 | 0.176988 | 0.0252  |           |
| Mean | 0.135612 |          | 0.03948 | 0.50579   |
| Sigma | 0.021273 |         | 0.016844 | 0.02795  |
| C.V. | 15.69%   |          | 42.66%  | 5.53%     |

EXAMPLE II

A glass flow cell with a magnetically formed stainless steel screen are prepared as in Example I.

For a competition assay for digoxin, PMMA beads are coated with digoxin using digoxin conjugated to a protein such as bovine serum albumin (BSA), which acts as a sticky carrier causing the less sticky digoxin to adhere to the beads. Fluorescently labeled anti-digoxin antibody is diluted in PBS.

Digoxin/BSA coated PMMA particles, suspended in PBS are flowed into the conduit and allowed to accrete against the stainless steel porous screen. Sample, either positive (containing digoxin) or negative is prepared, mixed with fluorescently labeled anti-digoxin antibody, and allowed to incubate. The mixture is flowed through the conduit. In the case of negative samples the fluorescently labeled antibody binds to the digoxin on the PMMA particles and is retained. In the case of positive samples, digoxin in the sample binds with some of the labeled antibody and this conjugate flows through the PMMA particles and stainless steel screen without being retained. PBS solution is flowed through the capillary to wash the beads and remove unbound labeled antibody. Signals are calculated as in Example I, but in this case a low analyte level in the sample gives a high signal.

Since certain changes may be made in the above process and apparatus without departing from the scope of the invention herein involved, it is intended that all matter contained in the above description or shown in the accompanying drawing shall be interpreted in an illustrative and not in a limiting sense.

What is claimed is:

1. A flow cell for use with a fluid sample comprising, in combination:

elongated conduit means;

a mass of paramagnetic particles disposed in said conduit means; and means for establishing within said conduit means a gradient of magnetic flux density, said means being selected, and being positioned relative to said conduit means, so that said gradient is sufficient to cooperate with said mass of paramagnetic particles to form a substantially self-supporting fluid-porous screen spanning the cross-sectional area of said conduit means, whereby, when a fluid sample containing particulates is flowed through said conduit, said screen mechanically separates those particulates having a predetermined size from said fluid sample and supports said separated particulates of predetermined size in said conduit.

2. A flow cell as defined in claim 1 wherein said establishing means produces a magnetic field that includes vector components disposed transversely to the axis of elongation of said conduit means.

3. A flow cell as defined in claim 1 wherein said establishing means comprises means for providing at least a pair of magnetic pole faces disposed on opposite sides of said conduit means so as to provide a magnetic field gradient along the axis of said conduit means.

4. A flow cell as defined in claim 3 wherein said establishing means produces said gradient of magnetic flux density electromagnetically.

5. A flow cell as defined in claim 3 wherein said establishing means comprises at least a pair of permanent magnets.

6. A flow cell as defined in claim 1 wherein individual particles within said mass of paramagnetic particles have immobilized on surfaces thereof, at least a moiety of a ligand/conjugate complex.

7. A flow cell as defined in claim 6 wherein said ligand/conjugate complex includes a tag capable of emitting electromagnetic radiation responsively to excitation radiation.

8. A flow cell as defined in claim 6 wherein said paramagnetic particles are substantially light-reflective.

9. A flow cell as defined in claim 1 further including:

a porous mass of beads disposed in said conduit means and supported by said screen, the porosity of said mass of beads being selected to permit fluid flow of said sample therethrough, individual beads of said mass having immobilized on surfaces thereof at least a moiety of a ligand/conjugate complex.

10. A flow cell as defined in claim 9 wherein said at least a moiety of a ligand/conjugate complex includes a tag capable of emitting electromagnetic radiation responsively to excitation radiation.

11. A flow cell as defined in claim 9 wherein individual beads in said porous mass of beads are substantially light-transparent.

12. A flow cell as defined in claim 9 wherein said paramagnetic particles are selected within a range of cross-sectional sizes such that the porosity of said screen is large enough to allow free flow of sample fluid and its constituents through said screen while arresting flow of said beads therethrough.

13. A flow cell defined in claim 1 wherein at least a portion of said conduit is light-transparent.

14. A flow cell as defined in claim 13 wherein said screen is maintained at least adjacent said light-transparent portion solely by interaction with said gradient of magnetic flux density.

15. A flow cell as defined in claim 13, further including a porous mass of beads disposed in said conduit means and having immobilized on surfaces thereof at least a moiety of a ligand/conjugate complex, said beads being dimensioned within a specified range of diameters, and wherein, the porosity of said screen is sufficiently smaller than said range so that said beads, when entrained in a fluid flow, are trapped by said screen within said light-transparent portion.

16. In a method comprising providing a plurality of beads dimensioned within a specified range of diameters; flowing a suspension of said beads through a conduit; and arresting the flow of said beads through said conduit by a fluid-porous screen having pores of lesser diameter than said range, so that said beads accrete substantially at said screen to form a porous mass; assaying a fluid sample, including flowing at least said fluid sample through said porous mass of beads, so as to provide a reaction therewith on surfaces of said beads; the improvement including steps of:

introducing, prior to flowing said suspension of beads through said conduit, a plurality of paramagnetic particles into said conduit; and establishing within said conduit a gradient of magnetic flux density sufficient to cause said plurality of paramagnetic particles to form said fluid-porous screen, said fluid-porous screen formed by said paramagnetic particles being substantially self-supporting.

17. A method of assaying a fluid sample, the method comprising steps of:

introducing a plurality of paramagnetic particles into a fluid-flow conduit;

establishing within said conduit a gradient of magnetic flux density sufficient to cause said plurality of paramagnetic particles to form a substantially self-supporting fluid-porous screen spanning the cross-sectional area of said conduit means;

assaying a fluid sample, including flowing at least said fluid sample through said screen, so as to provide a reaction with at least a component of said fluid sample on the surfaces of said paramagnetic particles, whereby, when said fluid sample contains particulates, said screen mechanically separates those particulates having a predetermined size from said fluid sample and supports said separated particulates of predetermined size in said conduit.

18. A method of assaying a fluid sample comprising the steps of:

providing a fluid-flow conduit lacking any mechanical support means within said conduit means;

introducing into said conduit a plurality of paramagnetic particles;

establishing within said conduit a gradient of magnetic flux density sufficient to cause said plurality of paramagnetic particles to form a substantially self-supporting fluid-porous screen spanning the cross-sectional area of said conduit; introducing a plurality of beads, so that said plurality of beads accrete substantially on said screen to form a porous mass of beads; and flowing at least said fluid sample through said conduit, through said porous mass of beads and through said screen, so as to provide a reaction with at least one component of said fluid sample on the surfaces of said porous mass of beads.

* * * * *

UNITED STATES PATENT AND TRADEMARK OFFICE
CERTIFICATE OF CORRECTION

PATENT NO. : 5,565,365
DATED : October 15, 1996
INVENTOR(S) : Thomas R. Glass

It is certified that error appears in the above-indentified patent and that said Letters Patent is hereby corrected as shown below:

Column 1, line 52: please delete "patent application "; and insert therefor -- Patent Application --.

Column 3, line 58: please delete "patent application"; and insert therefor -- Patent Application --.

Column 3, line 59: please delete "07/924,720"; and insert therefor -- 07/924,720, --.

Column 7, line 5: please delete "ferdti.n"; and insert therefor -- ferritin --.

Column 10, line 1: please delete "sample,"; and insert therefor -- sample --.

Column 10, line 32: please delete "conduit;"; and insert therefor -- conduit, through which said fluid sample can pass; --.

Column 10, line 36: please delete "beads"; and insert therefor -- beads, --.

Signed and Sealed this

Twenty-fifth Day of February, 1997

Attest:

BRUCE LEHMAN

Attesting Officer        Commissioner of Patents and Trademarks